(12) United States Patent
Goldammer et al.

(10) Patent No.: US 9,367,903 B2
(45) Date of Patent: *Jun. 14, 2016

(54) METHOD AND APPARATUS FOR CORRECTING ARTIFACTS DURING GENERATION OF X-RAY IMAGES, IN PARTICULAR COMPUTED TOMOGRAPHY, OR RADIOGRAPHY BY MEANS OF TEMPORAL MODULATION OF PRIMARY RADIATION

(75) Inventors: Matthias Goldammer, München (DE); Karsten Schörner, München (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 253 days.

This patent is subject to a terminal disclaimer.

(21) Appl. No.: 14/009,298

(22) PCT Filed: Mar. 23, 2012

(86) PCT No.: PCT/EP2012/055202
§ 371 (c)(1),
(2), (4) Date: Oct. 1, 2013

(87) PCT Pub. No.: WO2012/130754
PCT Pub. Date: Oct. 4, 2012

(65) Prior Publication Data
US 2014/0056407 A1    Feb. 27, 2014

(30) Foreign Application Priority Data
Apr. 1, 2011 (DE) .......................... 10 2011 006 662

(51) Int. Cl.
| | | |
|---|---|---|
| G21K 1/10 | (2006.01) |
| G06T 5/00 | (2006.01) |
| A61B 6/00 | (2006.01) |
| G01N 23/04 | (2006.01) |
| G06T 11/00 | (2006.01) |
| G06T 5/50 | (2006.01) |
| A61B 6/03 | (2006.01) |

(52) U.S. Cl.
CPC ............... *G06T 5/003* (2013.01); *A61B 6/4035* (2013.01); *A61B 6/5205* (2013.01);
(Continued)

(58) Field of Classification Search
CPC ........ A61B 6/483; A61B 6/032; A61B 6/482; A61B 6/5258; A61B 6/5282; A61B 6/4035; A61B 6/405; G06T 1/1005; G01N 23/04; G21K 1/10
USPC ........................... 378/6, 7, 62, 98.4, 156, 158
See application file for complete search history.

(56) References Cited

U.S. PATENT DOCUMENTS

| | | |
|---|---|---|
| 5,533,088 A | 7/1996 | Fivez |
| 7,463,712 B2 | 12/2008 | Zhu et al. |

FOREIGN PATENT DOCUMENTS

| | | |
|---|---|---|
| DE | 24 54 537 | 5/1976 |
| DE | 102011006662.4 | 4/2011 |

OTHER PUBLICATIONS

Office Action for German Pat. Appl. 102011006662.4 dated Jan. 25, 2012.
(Continued)

*Primary Examiner* — Jurie Yun
(74) *Attorney, Agent, or Firm* — Slayen Grubert Beard PLLC

(57) ABSTRACT

Artifacts caused by scattered radiation when generating X-ray images of objects are corrected using a temporally alterable modulation of the primary radiation. A respective set of originally amplitude-modulated modulation projections of the object is generated and a respective scattered image allocated to the respective modulation projections is calculated. The method is particularly suitable for fast CT scans.

22 Claims, 9 Drawing Sheets

(52) U.S. Cl.
CPC ............ *A61B 6/5282* (2013.01); *G01N 23/04* (2013.01); *G01N 23/046* (2013.01); *G06T 5/002* (2013.01); *G06T 5/50* (2013.01); *G06T 11/005* (2013.01); *A61B 6/032* (2013.01); *G01N 2223/206* (2013.01); *G01N 2223/419* (2013.01); *G06T 2207/10116* (2013.01); *G06T 2207/10152* (2013.01); *G06T 2207/30004* (2013.01)

(56) References Cited

OTHER PUBLICATIONS

International Search Report for PCT/EP2012/055202; mailed Jul. 11, 2012.

L. Zhu et al; "X-ray scatter correction for cone-beam ct using moving blocker array"; Proceedings of SPIE; vol. 5745; pp. 251-258, 2005.

G. Kowalski, "Suppression of scattered radiation in radiography and improvement of resolution by spatially modulated intensity"; Applied Optics, vol. 15, No. 3, Mar. 1976, pp. 648-655.

H. Gao et al.; "Scatter correction method for x-ray CT using primary modulation: Phantom studies"; Med. Phys. vol. 37, No. 2, Feb. 2010; pp. 934-946.

J.-Y. Jin et al.; "Combining scatter reduction and correction to improve image quality in cone-beam computed tomography (CBCT)"; Medical Physics; vol. 37; No. 11; 2010; pp. 5634-5644.

P. Hammersberg et al.; "Correction for beam hardening artefacts in computererised tomography"; Journal of X-ray Science and Technology; vol. 8; 1998; pp. 75-93.

J. Wang et al.; Scatter correction for cone-beam computed tomography using moving blocker strips: A preliminary study; Medical Physics; vol. 37; No. 11; Nov. 2010; pp. 5792-5800.

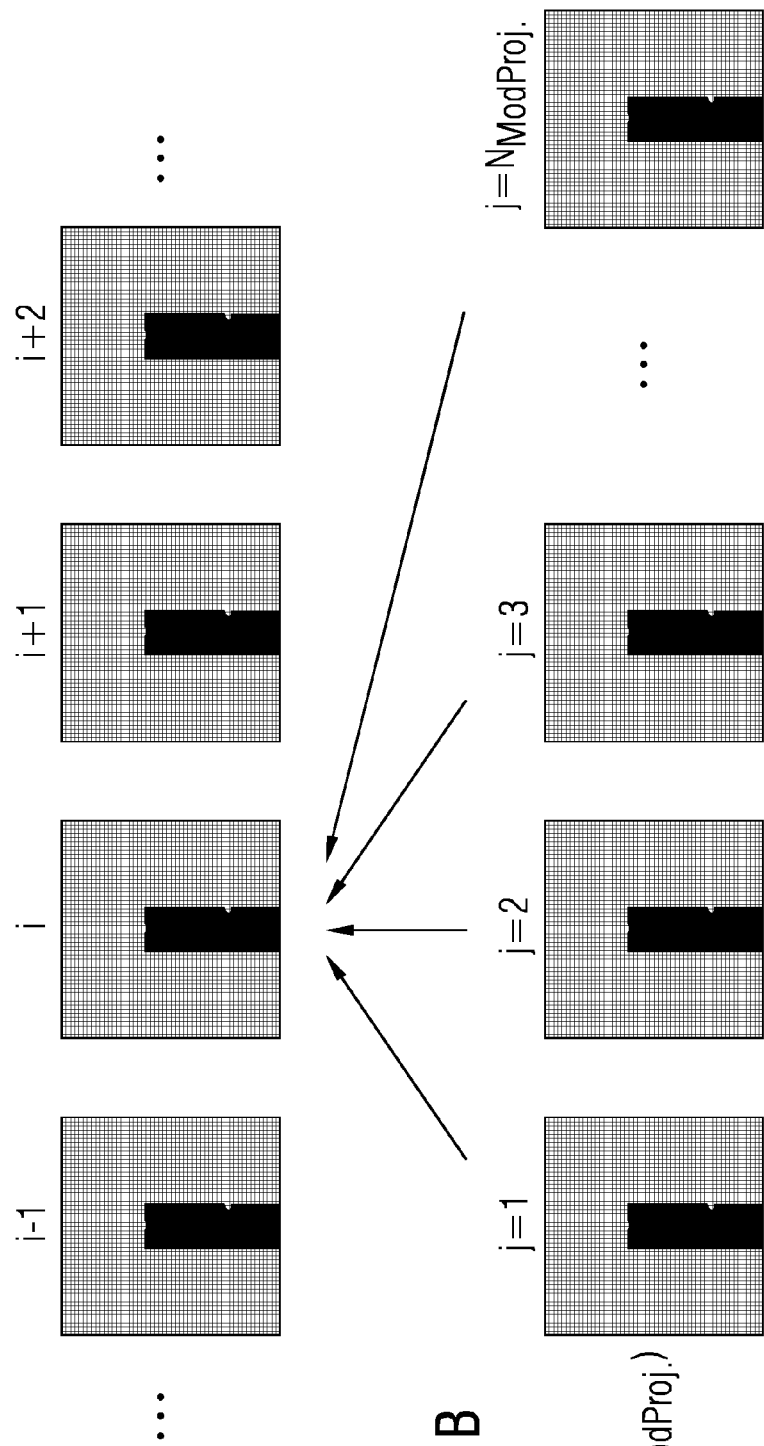

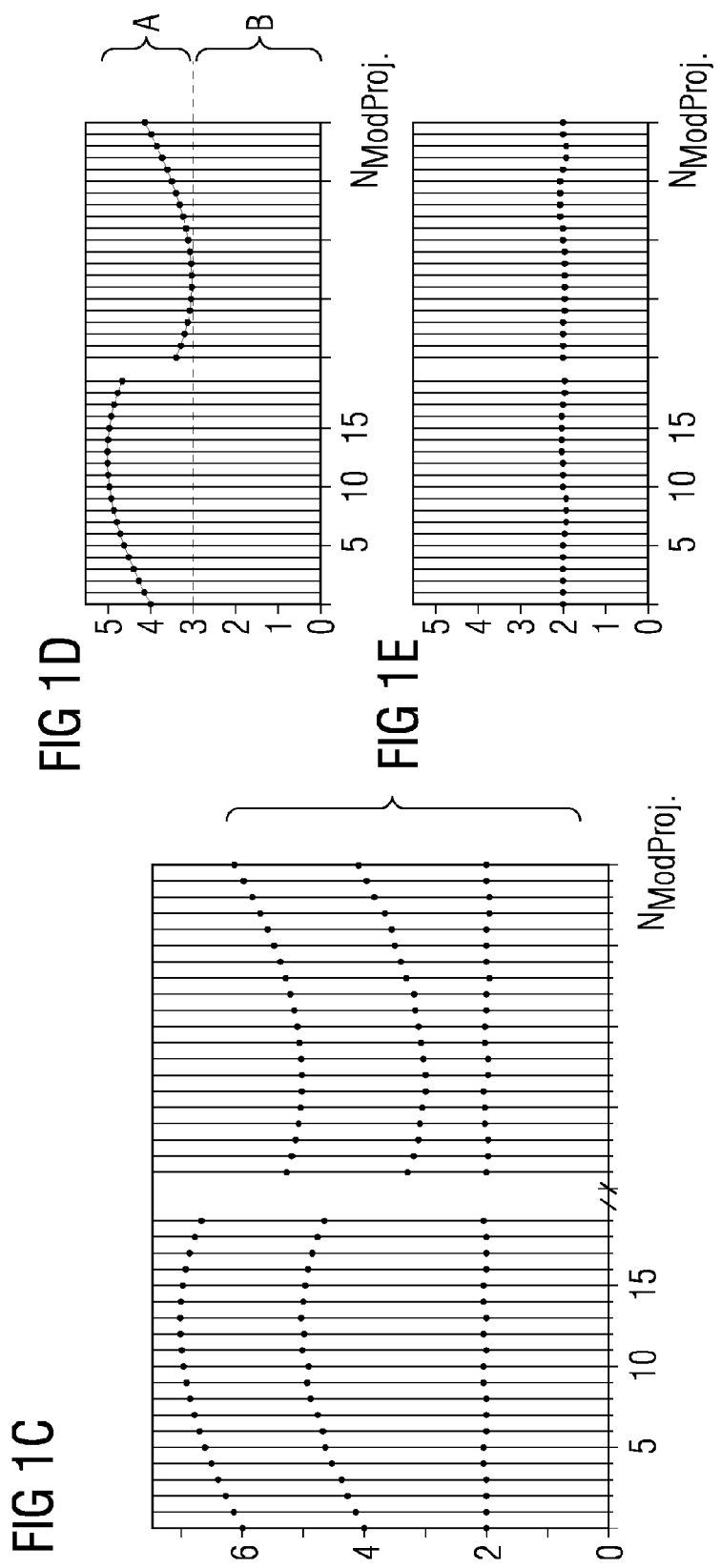

METHOD AND APPARATUS FOR CORRECTING ARTIFACTS DURING GENERATION OF X-RAY IMAGES, IN PARTICULAR COMPUTED TOMOGRAPHY, OR RADIOGRAPHY BY MEANS OF TEMPORAL MODULATION OF PRIMARY RADIATION

CROSS REFERENCE TO RELATED APPLICATIONS

This application is the U.S. national stage of International Application No. PCT/EP2012/055202, filed Mar. 23, 2012 and claims the benefit thereof. The International Application claim the benefit of German Application No. 10 2011 006 662.4 filed Apr. 1, 2011, both applications are incorporated by reference herein in their entirety.

BACKGROUND

In X-ray computed tomography (CT), scattered radiation occurs as well as the primary radiation that is to be detected. If the detection of scattered radiation is not prevented, or if the recorded projections are not corrected, this leads to scattered radiation artifacts in the reconstructed CT volume, which consists of voxels. Such scattered radiation artifacts can, for example, be caused by a so-called cupping effect, which leads to unequal voxel values in a homogeneous object material, such that a curve rather than a straight line arises when the density values are applied along a line, so when a line profile is established. In addition, striped patterns and losses in contrast can generally occur. Scattered radiation also arises in the field of digital radiography and above all causes losses in contrast here.

There exist various known methods of resolution for scattered radiation correction, which can primarily be separated into two groups:
1. Measures for the reduction in detected scattered radiation, such as is carried out, for example, by using an anti-scatter grid.
2. So-called a posteriori corrections of the scattered radiation by subtracting the scattered proportion accordingly in each CT projection.

For the second group, it is necessary to have as accurate a knowledge as possible of the detected scattered proportion. For this, various approaches exist for determining this scattered proportion, which can also be separated into two groups:
1. Software-based solutions, which can be, for example, Monte Carlo simulations, deterministic calculations of first-order scattering, convolution algorithms based on so-called point spread functions.
2. Experimental methods for determining the scattered proportion by measurements.

Within this second group of experimental methods, different measuring procedures are known. For example,
a) beam-stopper-based methods and
b) a technique that is complementary thereto, which uses apertures and even so-called beam holes, and
c) a method that has only been proposed recently, which is based on so-called primary modulation.

As regards the most recent method, the following related art is known.

U.S. Pat. No. 7,463,712 B2 discloses scattered radiation correction for the generation of an X-ray image, wherein a direction-dependent modulation of the primary X-rays is used, which leads to a location-dependent modulation on the detector of the primary radiation. Scattered radiation in an X-ray image generation system having an X-ray source and an X-ray detector is corrected by using amplitude modulation for translating the spatial frequency of a detected X-ray to a higher frequency and by filtering out the low-frequency scattered radiation. One way to obtain the low-frequency primary signal without scattered radiation is by demodulation.

The decisive advantage of a method that uses primary modulation over many other known experimental methods is that the scattering measurement and scattered radiation approximation can hereby be carried out within the actual CT scan, i.e. the scattered data is extracted at the same time as the actual CT projections. Compared to other known methods, which require an additional measuring process, this leads to less measuring expenditure and at the same time to time being saved, which represents a decisive improvement for X-ray CT in particular. In addition, radiation dosage is also saved compared to measuring methods wherein an additional measuring process is required.

The method disclosed according to U.S. Pat. No. 7,463,712 B2 is based on a spatial primary modulation. As a result of high image frequencies, which are caused in particular by hard transitions in the image caused by edges of the object to be recorded, there arises in the frequency domain an overlap of the spectral copy of the primary information with the unmodulated frequency information. This renders a clean demodulation of the primary image more difficult. This problem is partially solved by a proposed, so-called "boundary detection". Furthermore, in the maximum resolvable (image) frequency for the reconstruction of the primary image, and thus also for that of the scattered image, one is limited by the fixed, spatial modulator frequency. The maximum image frequency that can be reconstructed for the scattered image thus lies at half the modulator frequency. An unmoved primary modulator that is used here often leads to ring artifacts in the reconstructed CT volumes.

The known method according to U.S. Pat. No. 7,463,712 B2 provides that a primary modulator is placed between the object to be recorded and X-ray tubes. The primary modulator imprints a pattern onto the primary rays by amplitude modulation, for example in the form of a chess-board with light and dark fields. To that end, a circuit board made from copper can be used, for example, into which a pattern is introduced by an etching process, i.e. the copper is etched away accordingly on the light fields. The attenuation properties or attenuation coefficients of copper or of the bare circuit board material, which have different strengths, ensure a corresponding radiation attenuation through the dark fields (copper), whereas hardly anything or nothing at all (as regards circuit board material) is attenuated on the light fields. During the entire CT scan or the entire CT scanning, the modulator is located in a stationary, i.e. unmoved, position between the object and X-ray tube, i.e. it does not change its position. The modulated, chess-board-like pattern is thus to be found again in every projection of the CT scan, i.e. both in the radiation region and in regions covered by the object. Here, the relative modulation strength that addresses the primary signal is the same size at all positions. However, it is not only this modulated primary signal that is recorded by the detector, but this is also superimposed by an unmodulated, spatially low-frequency scatter signal, which comes about as a result of X-ray scattering effects, in particular Compton scattering processes, in the test object and in the laboratory environment. The detector therefore receives a complete signal formed by the modulated primary signal and the superimposed, unmodulated scattering signal.

It is hereafter possible to separate the modulated primary signal in the Fourier space from the unmodulated scattering signal. This takes place via a corresponding high-pass or low-pass filtering of the modulated projection. In the frequency domain, the low-pass-filtered version of the modulated projection results in the superimposition of the frequency proportions of unmodulated primary image and scattering function. The high-pass-filtered version contains only the spectral components of the modulated primary signal, so can later be demodulated and weighted so as to obtain an approximation of the sole primary signal in the frequency domain. After inverse Fourier transformation, this can be subtracted as an approximated primary image of the low-pass-filtered version, which has scattering and primary signals, so as to obtain an approximation of the scattered image. It is noted that, in the method described herewith, a so-called edge detection and edge smoothing are applied to each modulated projection, which is also described as boundary detection. Such a smoothing considers that high-frequency image proportions are already present as a result of the object alone and in particular due to the object edges. This is independent of each modulation. These high-frequency, unmodulated proportions overlap with the spectral copies of the modulated primary signal in the Fourier space. Mixing modulated and unmodulated signals has, as a consequence, an incorrect demodulation of the primary signals if this is not corrected. This means that, in particular in the object edge regions and also in the interior of the object, which is then described in this context as "spilling", it leads to artifacts and a false reconstruction of the primary image. These effects also have an effect on the scattered image generated later. To absorb or suppress such high-frequency image proportions, which are in particular caused by object edges, the so-called boundary detection is applied, which finds object edges and smoothes them accordingly using a Gaussian filter. The significant artifacts caused by the high-frequency, unmodulated image proportions, are indeed hereby reduced; however, there arises imprecision in the edge region at such points, since the Gaussian filter is later rendered no longer retrogressive. The scattered image extracted in this way is now correspondingly removed from the CT projections. Since the modulation pattern is now still present in the projections, the CT projections are normalized to the radiation intensity according to the modulator. In this way, the modulator pattern in the projection image can then be removed. This takes place using division by recording the modulator without further objects in the beam path. Such a recording can also be described as reference measurement. It is noted that beam-hardening effects occur as a result of the modulator and indeed in particular due to the dark copper fields. If such effects remain uncorrected, there first arises an erroneous scattering approximation and then an incomplete removal of the chess-board pattern in the last-mentioned division step. Due to the stationary modulator, this can have ring artifacts in the CT cross-sectional images as a consequence. The fact that beam-hardening effects exist and lead to the cited errors is, for example, known from "Korrektur von Strahlaufhärtungsartefakten bei der Computertomographie" (Correction of beam-hardening artifacts in computed tomography) by Peter Hammersberg and Mans Mangard in the Journal für Röntgen-Wissenschaft and Technologie 8 (Journal for X-ray science and technology, volume 8), IOS Press, 1998, pages 75-93.

Hammersberg and Mangard disclose that exact density measurements are rendered more difficult during the use of polyenergetic X-ray sources as a result of beam hardening based on erroneous gradients of linear attenuation coefficients in computed tomography cross-sectional images. A corrective method is described wherein polyenergetic computed tomography data is converted into monoenergetic computed tomography data. Computed tomography data is derived as a function of the object thickness from measured data points and is depicted as a polynomial. The polyenergetic computed tomography data is simulated exactly by simulation based on the object material density, the object material composition, the X-ray energy spectrum, the detector response and the information transfer from the detector to digitalized data. The curved line of the function representing the polyenergetic computed tomography data can be determined exactly by a polynomial to the eighth order or higher, or by cubic spline interpolation.

SUMMARY

Described below are a method and an apparatus for X-ray image generation, in particular computed tomography, or digital radiography, in such a way that artifacts produced as a result of scattered radiation are corrected more simply and effectively compared to the related art in a reconstructed computed tomography volume. Such artifacts can be, for example, cupping effects, striped patterns and/or losses in contrast. Furthermore, an artifact of beam hardening caused by primary modulation is, in addition, to be simply and effectively corrected. For example, contrast improvement in comparison with known methods is to be effected.

According to a first aspect, a method for correcting artifacts in an X-ray projection of an object is provided, wherein X-rays of a primary X-ray source is charged with a repeating pattern of regions with different X-ray signal strengths, is thus amplitude modulated, then run through the object to be imaged to a detector, is here detected as a complete signal, and from this a scattered image is calculated, which is separated from an original, amplitude-modulated projection. The method is characterized in that the X-rays of the primary X-ray source generates primary signals and these are amplitude modulated with temporal alterations, such that a number $j=1 \ldots N_{Mod}$ is generated from modulation projections allocated to a respective point in time.

According to a second aspect, an apparatus for correcting artifacts in an X-ray projection of an object is provided, wherein X-ray radiation of a primary X-ray source is run through a modulator field with a repeating pattern of regions with different X-ray attenuation, is amplitude modulated here, then run through the object to be imaged to a detector, detected there and a scattered image is calculated from this, which is separated from an original, amplitude-modulated projection, wherein the modulator field has a repeating pattern, the first half of which is congruent to a second half, regions of both halves, which are congruent to each other, have X-ray attenuation coefficients that are opposite to each other, the pattern is repeated along at least one repeating line and a length of the pattern along the repeating line corresponds to a period length. The apparatus is characterized in that a displacement apparatus displaces the modulator field with respect to a relative movement of the X-ray source, the object and the detector, on the one hand, and the modulator field, on the other, from a first relative position to a second relative position along the repeating line at a respective odd-number multiple of half a period length, in such a way that modulator field regions with small and relatively large X-ray attenuation coefficients thereto are mutually exchanged.

A modulator field operating as a primary modulator extends along a plane and has thicknesses that correspond to the modulator material.

Opposite X-ray attenuation coefficients mean, for example, a large and a relatively small X-ray attenuation coefficient compared thereto. A value range of normalized X-ray attenuation coefficients is determined by these values being able to be, in particular, greater than or equal to zero and less than or equal to one.

Modulation projection image fields arise, which have been generated by relatively large X-ray signal strengths, which can be denoted as light fields. Modulation projection image fields that have been generated by smaller signals compared to the large X-ray signal strengths can be denoted as dark fields. High radiation intensity generates a large signal, high grey tone. Low radiation intensity generates a smaller signal, so a smaller grey tone.

A repeating line of the pattern of the modulator field is a line along which the pattern repeats. A length of a repeating line in a pattern corresponds to a period length. A repeating line can be a straight line.

Advantageously, due to dark grid fields, ring artifacts generated in a static primary modulator can be effectively reduced according to the solution.

Furthermore, a moved primary modulator has the significant advantage over a stationary primary modulator that any remaining pattern of the primary modulator that has not been completely compensated for is distributed evenly to the complete volume or evenly over a CT cross-section during a rear projection process of the reconstruction. In this way, typical ring artifact effects, such as those which occur with a stationary modulator, can be avoided. In this way, a subordinate use of algorithms for the suppression of ring artifact effects, as is described according to U.S. Pat. No. 7,463,712 B2, is also only optional.

Accordingly, the following advantages arise: The problem is solved by an overlapping of modulated and unmodulated frequency regions being avoided during the temporal modulation, since the useful signal, which corresponds to an attenuation of the primary signal through the object, is temporally constant and thus limited to a frequency of =0. Furthermore, a method for each detector pixel can be individually embodied. In this way, the maximum resolvable frequency can be raised up to the maximum frequency predetermined by the detector. This means that the maximum resolution for the generation of the scattered image is available. Furthermore, to avoid ring artifacts, potential remaining defects, for example as a result of an insufficient beam-hardening correction or during the division of the modulator projection through the reference projection without an object, can be distributed equally to the complete volume or over a CT cross-section during the rear projection process of the reconstruction, such that typical ring artifacts, such as those that occur when there is an unmoved modulator, hardly occur or do not occur at all. Thus, a subsequent application of algorithms to suppress ring artifacts is also only optional.

Accordingly, a temporally modulated signal can be provided and processed simply in a particularly advantageous manner for a respective pixel.

According to an advantageous embodiment, the primary X-ray source can have individually activateable matrix regions which, at a previous point in time according to the pattern, emit a small or a relatively large X-ray signal strength, and at a subsequent point in time emit the respective other X-ray signal strength, and at every point in time a respective original amplitude-modulated modulation projection of the object is generated and a respective scattered image allocated to this modulation projection is determined.

According to a further advantageous embodiment, a modulator field having regions corresponding to the pattern with a small or a relatively large X-ray attenuation thereto can be arranged in the beam path from the X-ray source to the object, and X-ray source, object and detector on the one hand, and the modulator field on the other, are moved from a previous position to a subsequent position relative to each other and thus modulator field regions with small and relatively large X-ray attenuation coefficients thereto are mutually exchanged in the X-ray beam path, a respective original amplitude-modulated modulation project of the object is generated in each of the two positions and a respective scattered image allocated to these modulation projections is determined. A scattered image arises from a set of modulation projections j=1 . . . N_ModProj. This can later be removed individually from the modulation projections before these are then BHC-corrected (BHC=beam-hardening correction) and separated by the modulation function.

Intermediate levels are also conceivable as well as maximum levels, i.e. completely dark or completely light field, so a real modulation according to a sine course. This could be achieved, for example, by a gradually shaped primary modulator, so not only chess-board patterns, but also more refined gradations between the fields.

According to a further advantageous embodiment, a scattering signal of a detector pixel or a scattered image of a detector is obtained by subtracting a primary signal or primary image that has been demodulated after the temporal modulation from the complete signal or complete image.

According to a further advantageous embodiment, the demodulation is carried out by multiplying the recorded, partially modulated complete signal with a modulation function. This corresponds to a multiplication of temporal signals. Accordingly, frequencies based on temporal signals after corresponding Fourier transformation are generated, which are temporally applied.

According to a further advantageous embodiment, a subtraction of the scattered image assigned to the modulation projection, which takes place to provide a scatter-corrected modulation projection, can be carried out by a corresponding original modulation projection that has not been underscanned.

According to a further advantageous embodiment, a division of the scatter-corrected modulation projection carried out for the provision of an additionally modulation-corrected modulation projection is effected by a temporal modulation function that is determined without the object.

According to a further advantageous embodiment, generation of a respective scatter-corrected or scatter and modulator-field-corrected modulation projection can be embodied for a respective number j=1 . . . $N_{Mod}$ of modulations with subsequent averaging for increasing a signal-to-noise ratio.

According to a further advantageous embodiment, the previous and subsequent modulation can generate a respective modulation projection j=1 and j=2 and then the X-ray source and detector on the one hand and the object on the other can be rotated, after each second modulation projection, relative to each other around an axis of rotation in a rotational direction at an angle of rotation from a relative position i to a relative position i+1.

Accordingly, a construction of a modulator-free complete image is not necessary. This is justified on the grounds that a modulation and demodulation is not carried out between the spatial/image domain and the corresponding frequency domain, but rather a temporal modulation is carried out in such a way that the domains are the temporal and corresponding frequency domain.

According to a further advantageous embodiment, underscanning can be embodied for the calculation of a scattered image that is allocated to a modulation projection. According to a method, the scattered image can be detected pixel-accurately. An underscanning or downsampling of the modulation projections can optionally take place beforehand for noise suppression. Due to the temporal modulation and demodulation, given spatial frequencies are removed, i.e. the spatial modulation frequency predetermined by a primary modulator. As a result of this, a pixel-accurate calculation of a scattering value can be embodied.

According to a further advantageous embodiment, the complete signal, which is in particular partially modulated, can, per pixel, be classified as a temporal signal over all modulation projections j=1 . . . N_ModProj for the calculation of an approximated primary image allocated to a modulation projection, which image has individual primary signals, and can be high-pass filtered, whereby unmodulated proportions are omitted. A large part, for example approx. 80% of the primary signal, is unmodulated, wherein reference is made to signal B in FIG. 1d, as well as the complete scattering signal, wherein FIG. 1e depicts this recording; then this is demodulated by multiplication with the respective modulation function suitable for the pixel, which can be recorded without an object, and can then be low-pass filtered.

According to a further advantageous embodiment, the demodulated primary image allocated to the modulation projection can be subtracted from the complete image to calculate a scattered image assigned to a modulation projection. In this case, an averaged complete image can be used, which arises by adding the modulation projections and corresponding weighting. A demodulated primary signal of a pixel can be subtracted from a complete signal of the pixel. A complete signal can be obtained by averaging all complete signals on this pixel for all modulation projections. All scattering signals for the pixels are assembled into a scattered image, which can be subtracted from the modulation projections and further processed.

According to a further advantageous embodiment, an approximated scattering value can be subtracted from a measured, uncorrected intensity value for beam-hardening correction for a respective modulation projection image field, which has been generated by a relatively small X-ray signal strength; this difference corresponds to a first intensity value, which can be allocated to a corresponding penetrated object length by a corresponding intensity attenuation curve; this can be allocated to a second intensity value by an intensity attenuation curve for a modulation projection image field, which has been generated by a relatively high X-ray signal strength, to which intensity value the approximated scattering value can be re-added.

According to a further advantageous embodiment, the approximated scattering value can be determined from a calculated scattered image of a previous original modulation projection.

According to a further advantageous embodiment, the beam-hardening correction can be embodied during under-scanning.

According to a further advantageous embodiment, the beam-hardening correction can be embodied by a temporal modulation function, which is determined without the object, before the division of the scatter-corrected modulation projection.

According to a further advantageous embodiment, the displacement apparatus and a rotational apparatus can be synchronized with each other in order to rotate the object around an axis of rotation in a rotational direction at respective angle of rotation steps.

According to a further advantageous embodiment, the pattern can be a linear, square, wave-like or radial pattern.

According to a further advantageous embodiment, X-ray attenuation coefficients can be changed continuously and consistently from transitions of the modulator field regions with small X-ray attenuation coefficients to those with relatively large X-ray attenuation coefficients.

According to a further advantageous embodiment, modulation strengths of the modulator field regions with a relatively large X-ray attenuation coefficient can effect a complete signal reduction in a range of 10% to 30%.

According to a further advantageous embodiment, the modulator field can have regions with a small and relatively large X-ray attenuation coefficient thereto, as well as with additional X-ray attenuation coefficients.

BRIEF DESCRIPTION OF THE DRAWINGS

These and other aspects and advantages will become more apparent and more readily appreciated from the following description of the exemplary embodiments, taken in conjunction with the accompanying drawings of which:

FIG. 1A is a depiction of i CT projections onto a relatively moved object;

FIG. 1B is a depiction of j modulation projections, which are each allocated to a CT projection;

FIG. 1C is a graph of a discretely scanned recording of a complete signal;

FIG. 1D is a graph of a modulated and an unmodulated proportion of a primary signal from FIG. 1C;

FIG. 1E is a graph of a scattering signal of a primary signal from FIG. 1C;

DETAILED DESCRIPTION OF THE PREFERRED EMBODIMENT

Figure 2:
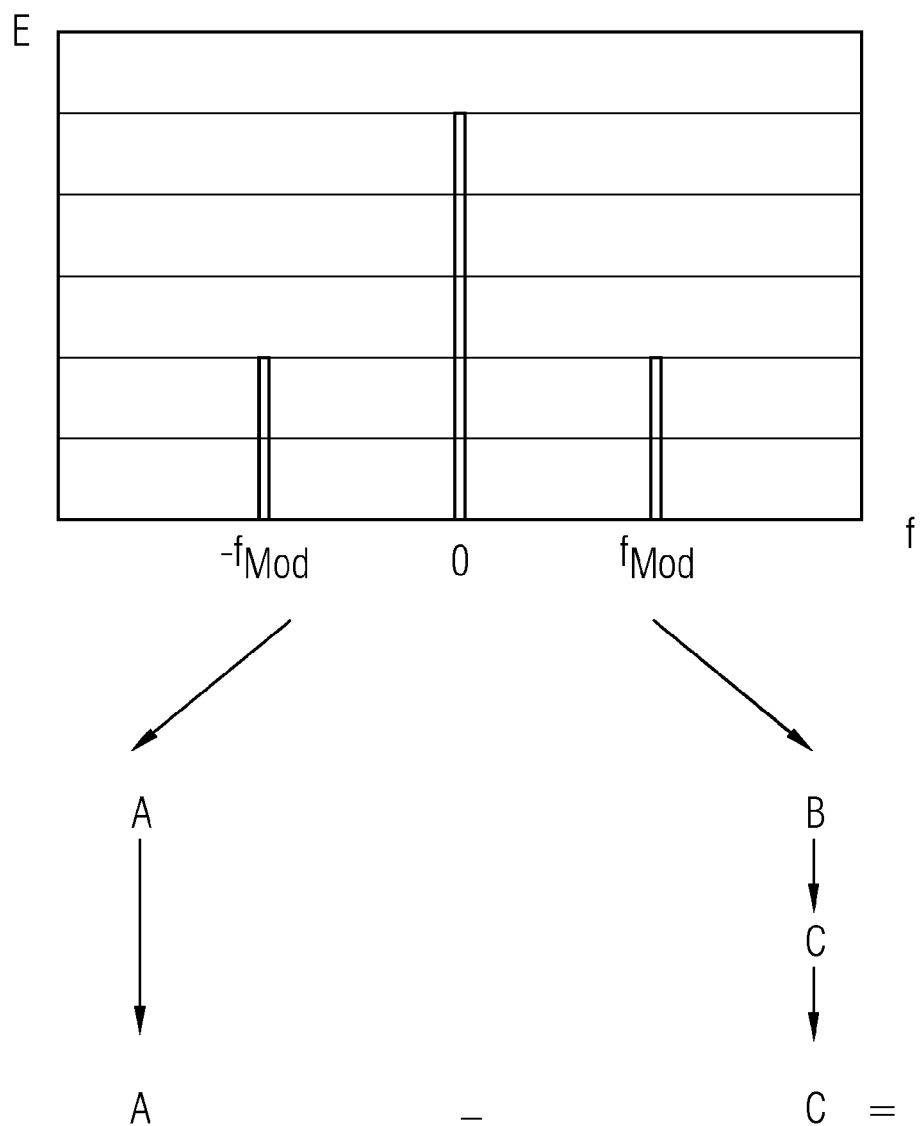
FIG. 2 is a graphic representation of an exemplary embodiment of a calculation of a scattering value for a pixel.

Reference will now be made in detail to the preferred embodiments, examples of which are illustrated in the accompanying drawings, wherein like reference numerals refer to like elements throughout.

FIG. 1A shows a depiction of CT projections onto a relatively moved object. A method for scattered ray correction is based on a temporal modulation of a primary signal. It is based on a CT scan or a CT scanning, wherein i=1 . . . $N_{Proj}$ CT projections are recorded. This means, for example, that the object to be subjected to tomography is rotated $N_{Proj}$ times, and indeed especially with industrial CTs, tubes and detectors are moved $N_{Proj}$ times and indeed especially with medical or industrial CTs for large objects, in order to penetrate the object that is to be subjected to tomography from $N_{Proj}$ different projection directions. The projected images are thus recorded two-dimensionally or one-dimensionally by a flat panel detector/array detector. Such a detector consists of pixels (x,y) where x=1 . . . $x_{Pix}$ and y=1 . . . $y_{Pix}$. For a further general description, only one pixel from this set is considered, which is described below as (x', y'). For the time being, beam-hardening effects are neglected, i.e. it is based on monochromatic radiation. An expansion to polychromatic radiation is undertaken in conjunction with FIG. 7. For scattered ray measurement, each CT projection i is divided into $N_{ModProj}$ individual projections, which can also be described as modulation projections. These individual projections are numbered all the way through with j, wherein j=1 . . . $N_{ModProj}$, and within which a temporal modulation of the primary signal takes place for each pixel (x, y).

FIG. 1B shows a depiction of j modulation projections, which are each allocated to a CT projection. With such a set of modulation projections, the object is stationary in an industrial CT or tubes and detectors are stationary in a medical CT, where stationary means unmoved. Only the primary signal is temporally amplitude-modulated, and indeed in such a way that the detected scattered proportion, which is primarily caused by Compton X-ray scattering processes, and indeed in particular in the object that is to be subjected to tomography and to a lesser extent due to the laboratory environment, changes as little as possible, as well as the spatial distribution thereof. The final requirement poses certain conditions on the technical implementation of the primary modulation.

FIG. 1C shows a depiction of a discretely scanned recording of a complete signal. For example, for a CT projection i, the plurality of modulation projections j=1 . . . $N_{ModProj}$ can now image the discrete or sampled or underscanned recording of the complete signal for each individual pixel (x', y'). The graphs in FIGS. 1C to 1E show a signal path in any given unit relative to the time in units of the j modulation projections. FIG. 1C depicts the temporal modulation of the primary signal that takes place in the respective modulation projections, considered for only one pixel (x', y'). The discrete recording of the complete signal includes the modulated primary and the overlapping, unmodulated scattering signal, as is depicted in FIGS. 1C to 1E. FIG. 1C shows a depiction of a discretely scanned recording of the complete signal for the pixel, wherein the complete signal, including primary and scattering signals, is depicted as the upper curve. The middle curve depicts the primary signal and the lower curve depicts the scattering signal. In FIG. 1D, a modulated and an unmodulated proportion of the primary signal from FIG. 1C is depicted. The modulated primary proportion is characterized by the letter A, and the unmodulated primary proportion is characterized by the letter B. FIG. 1E separately depicts the scattering signal, so a scattered proportion of a complete signal from FIG. 1C. A complete signal for a pixel (x', y') corresponds to the measured grey tone of this pixel.

FIG. 1E shows a depiction of a scattering signal, so a scattered proportion of a complete signal from FIG. 1C in a separate graph.

FIG. 2 depicts an exemplary embodiment of a calculation of a scattering value for a pixel. FIG. 2 depicts a spectrum of the Fourier-transformed complete signal of a pixel (x', y') in a graph having a frequency abscissa and an energy ordinate. Here, an energy proportion A at a frequency of 0 corresponds to a scattered proportion and an unmodulated primary proportion. An energy proportion B with a modulation frequency here corresponds to a modulated primary proportion. This energy proportion B is demodulated and weighted in accordance with a modulation strength, such that a demodulated, weighted primary signal C is obtained. The scattering value B can be calculated for the corresponding pixel (x', y') by the corresponding demodulation of the temporally modulated primary signal and by subsequent subtraction of this demodulated primary signal C from the measured complete signal A. All scattering values determined in this way for all pixels together produce the so-called scattered image. The scattered image can be removed from the j modulation projections after a corresponding processing, such as smoothing. The modulation projections are thus scatter-corrected. Only the temporal modulation of the primary signal is then still present for each individual pixel in the modulation projections. Due to a previous reference measurement without object, wherein only the temporal modulation function is recorded, these can now be divided out in the modulation projections. To improve a signal-to-noise ratio (SNR), the scatter and modulation-corrected projections are then averaged, since they all image the object that is to be subjected to tomography at the same position. In this way, a completely corrected CT projection i can be obtained.

FIGS. 3A to 5B show exemplary embodiments of a modulator field 3, in particular considered from the direction of a primary X-ray source. A temporal modulation of the primary signal can be embodied, for example, by a primary modulator moved relative to the object to be recorded. Such a primary modulator is a modulator field that has a corresponding radiation attenuation pattern. This can be a chess-board pattern, for example. Due to a corresponding displacement, for example in the horizontal or vertical direction, of this modulator field, the attenuation pattern can vary from light fields, i.e. no additional attenuation, to dark fields, i.e. a certain amount of radiation attenuation, for each pixel on the detector. However, this firstly only represents one potential embodiment; further embodiments are also possible, for example where radiation attenuations are generated in gradated intermediate steps.

Figure 3A:
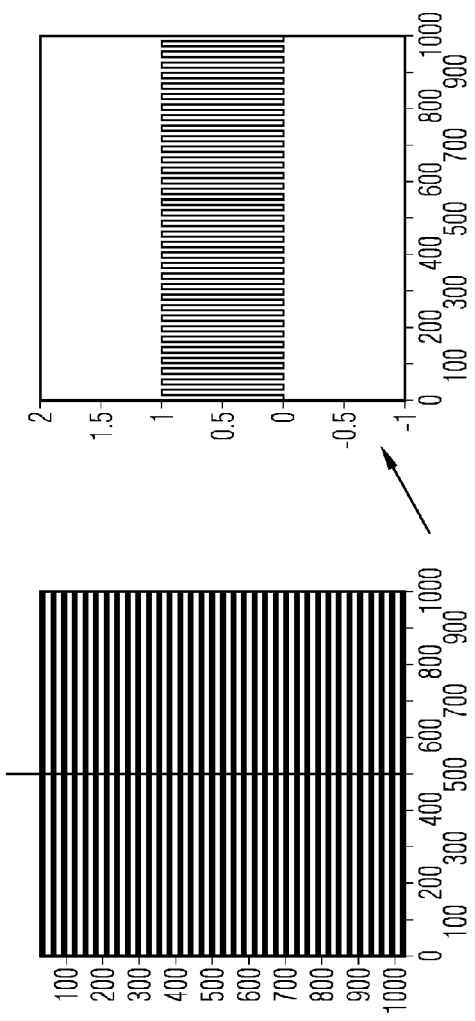
FIG. 3A to 5B are graphs of respective exemplary embodiments for a modulator field.

For example, FIG. 3A shows a linear pattern that is arranged horizontally or vertically and has hard transitions between fields. Such a modulator field has a rectangular grey-tone path, as is depicted in FIG. 3A on the right-hand side.

Figure 3B:
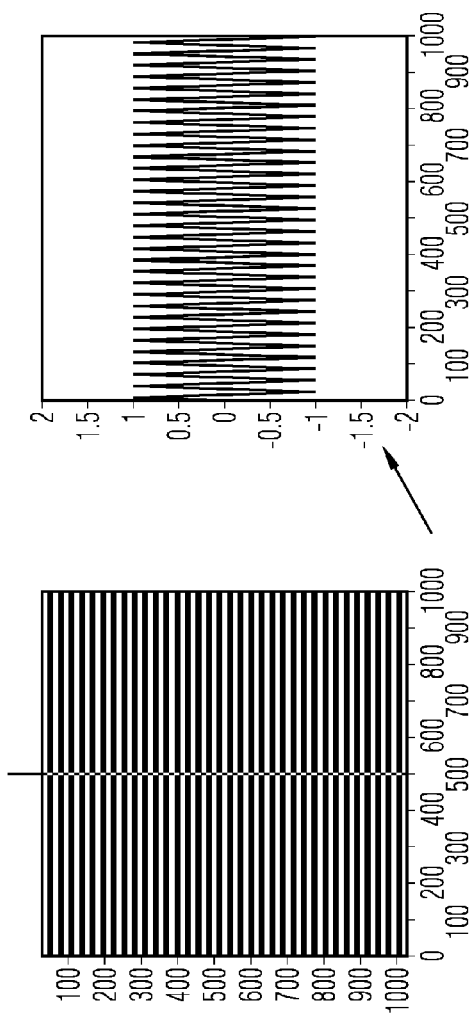

FIG. 3B shows a linear pattern that can be arranged horizontally or vertically, wherein such a linear pattern is arranged in wave form, i.e. transitions between regions of different X-ray attenuation coefficients are "soft". The corresponding sine-modulated grey-tone path is depicted on the right-hand side of FIG. 3B.

Figure 4A:
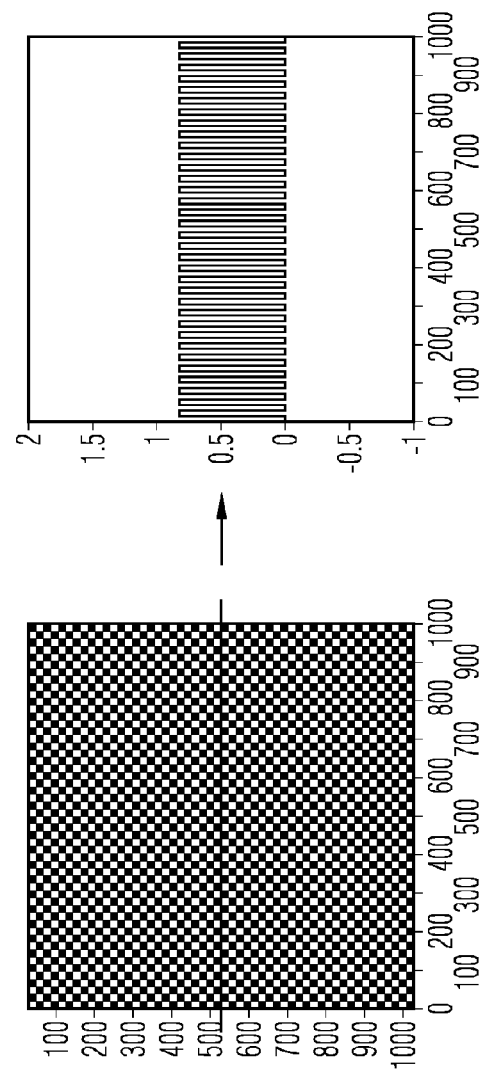

FIG. 4A shows a chess-board modulator field having "hard" transitions, i.e. the grey-tone path depicted on the right-hand side of FIG. 4A is rectangular.

Figure 4B:
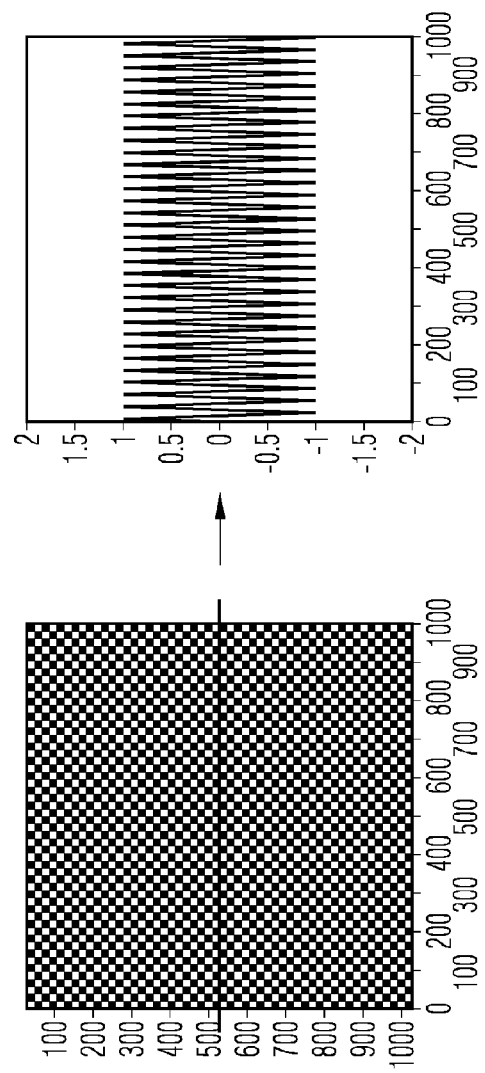

FIG. 4B shows a further chess-board modulator field having "soft" transitions, i.e. a grey-tone path depicted on the right-hand side of FIG. 4B is sine-modulated.

Figure 5A:
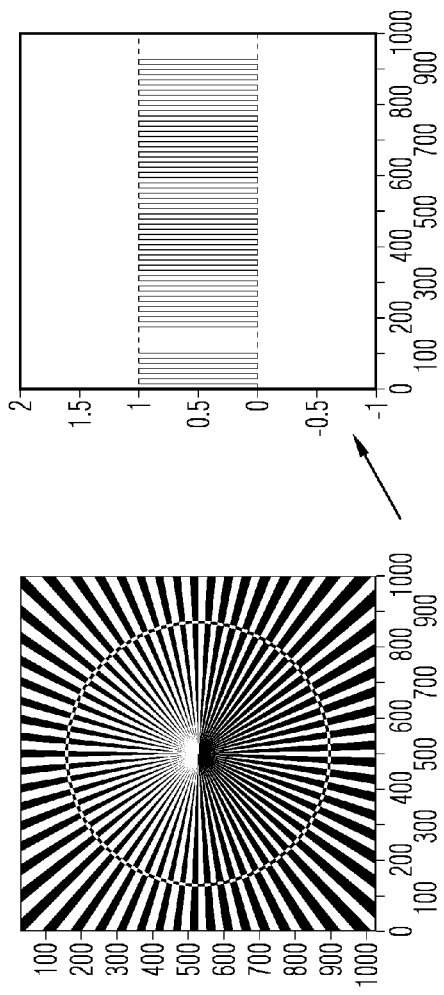

FIG. 5A shows a radial pattern that can be described as "chopper wheel", having "hard" transitions that arise from a rectangular grey-tone path depicted on the right-hand side of FIG. 5A.

Figure 5B:
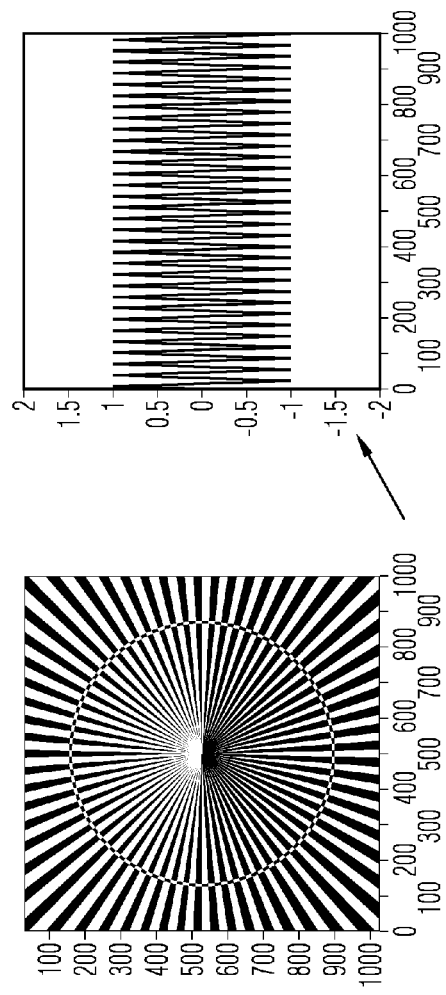

FIG. 5B shows a further exemplary embodiment of a modulator field having a radial pattern, wherein a sine-modulated grey-tone path is formed, such as is depicted on the right-hand side of FIG. 5B. When a radial pattern is applied, a displacement apparatus is provided as a rotational motor for the rotation of the modulator field around an axis of rotation. Various aspects for the construction of a primary modulator or modulator field are to be considered. A modulation strength specifies the strength with which there is maximum attenuation of a primary signal. Should there be a chess-board modulator, this corresponds to the thickness of the corresponding dark copper fields. The modulation strength on the one hand influences the accuracy with which the scattering values are approximated, and on the other hand it also establishes how much primary information is lost at these points. Since an improvement in the measuring accuracy of the scattering values means a decrease in primary information, i.e. an increase in noise, a compromise is to be selected here. Modulation strengths currently may be in the range from approx. 10 to 30% for the dark fields when there is reduction in the complete signal. Furthermore, it is considered that the primary modulator should be constructed in such a way that each pixel of the same added-up total intensity is released over the cited j modulation projections, in order to produce consistent behavior when looking towards the surface. This is not a necessary condition for correct measurement, but it simplifies the analysis of the total radiation. In this case, there can be calculation with the added-up intensity; otherwise, a further correction is necessary, which can be obtained by a measurement without object under exactly the same conditions. The most technically simple condition to implement is that of consistency if a displacement of the modulator field in the modulation projections exactly covers one period of the modulator. Furthermore, for a method, it is essential that a scattering distribution and a scattering distribution situation do not change as far as possible during a temporal modulation of a primary signal. This is because the alteration to the scattering situation within the j modulation projections leads to an increasingly erroneous approximation of the scattering values. With respect to primary modulators, it is particularly advantageous if it is ensured that the scattering distribution and the scattering distribution situation only change in as minor way as possible during a temporal primary modulation, when seen from a practical perspective. To that end, the primary modulation should take place as sparingly as possible and phase-shifted in adjacent regions. In an ideal case, the temporal primary modulation would take place individually for each pixel and thus with a phase shift to the degree of pi between adjacent pixels. In addition, the modulation strength should turn out as low as possible, although this is contrary to the effort of implementing as high a modulation strength as possible, in order to measure the scattering values as accurately as possible, as has been described above. Such specifications are, for example, virtually achieved by a relatively soft chess-board pattern with a modulation strength that is adapted to a desired noise. A modulation strength can thus be optimized by the noise. Between the extreme situations of there being an unusable, noisy scattered image and an unusable scattered image as a result of it having been changed too much, an optional strength can be selected, wherein the artifacts are minimized by scattering. This can, for example, be effected by simulation or test measurements with modulators of different strength.

Fundamentally, every technical measure for the temporal modulation of a primary signal is covered by the scope of protection of this application. A further embodiment of a temporal modulation can be provided in such a way that a controllable pattern is already imprinted on an X-ray beam within an X-ray source, which pattern can be temporally controlled and/or altered. It should be ensured that a modulation takes place as sparingly as possible, wherein a mere modulation of a complete tube current is, however, insufficient, since such a small area is not provided.

Figure 6:
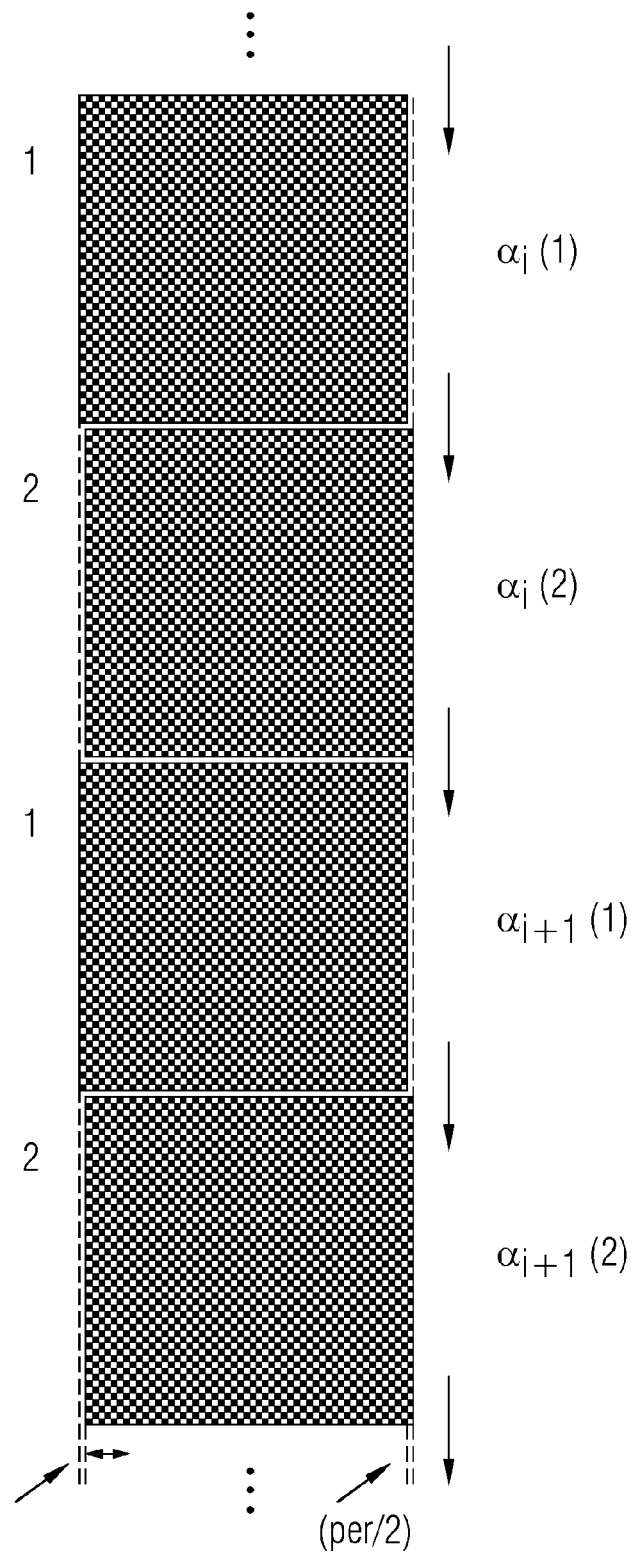
FIG. 6 is a graphic representation of an exemplary embodiment of modulator field movements and object movements relative thereto.

FIG. 6 shows an exemplary embodiment of a modulator field movement and object movement relative thereto; a movement or a displacement, which can be, for example, horizontal or vertical or diagonal, of the primary modulating modulator field is provided at half a period length per/2, and indeed in such a way that two projections displaced by per/2 are present for each angular position of the object that is to be subjected to tomography. To that end, the modulator field is not installed to be stationary, as is disclosed according to U.S. Pat. No. 7,463,712 B2, but rather is provided moveably on a motorized linear table to the degree of at least half a period length. Within a CT scan, the modulator field is then, for each angular position $\alpha i$ (i=1 ... n, wherein n means the number of angular positions to be recorded) of the object that is to be subjected to tomography after a first projected recording in a first modulator position 1 (projection $\alpha i(1)$), moved by half a period length in such a way that, when there is a chess-board modulator field, the dark field comes to lie where there were previously light fields, and vice versa. Then a second projection (with the second modulator position 2 (projection $\alpha i(2)$)) is recorded, wherein the object that is to be subjected to tomography has still not been moved. For the next angular position $\alpha i+1$ of the object that is to be subjected to tomography, and all those that follow, this twofold recording procedure with the first modulator field position 1 and the second modulator field position 2 is also repeated. The vertical arrows correspond to a timeline. This set of two modulation projections represents, pixel-by-pixel/for each individual pixel, the temporal modulation of the primary signal, superimposed with the least modulated scattering signal as possible. These complete signals are then respectively high-pass filtered, whereby the low-frequency scattered proportion is removed. There then takes place a demodulation by multiplying the high-pass-filtered complete signal with the corresponding modulation function, which provides an approximated primary signal as its result. In order to achieve a scattering signal, this approximated primary signal is removed from the added, weighted complete signal. The scattered image calculated is then subtracted from the original modulated CT projection that is in particular not underscanned. There then follows a pixel-by-pixel beam-hardening correction, which is described in greater detail below. The scattered beam and beam-hardening-corrected image can finally be divided by a pure modulator projection, i.e. without any object in the beam path, in order to correct the modulator pattern. The above-described operations are embodied for both projections $\alpha i(1)$ and $\alpha i(2)$ in the first modulator position 1 and the second modulator position 2. Since the object has not been moved in both of these projections, the scattered beam and beam-hardening and modulator-corrected projections are averaged so as to improve the signal-to-noise ratio (SNR).

Figure 7:
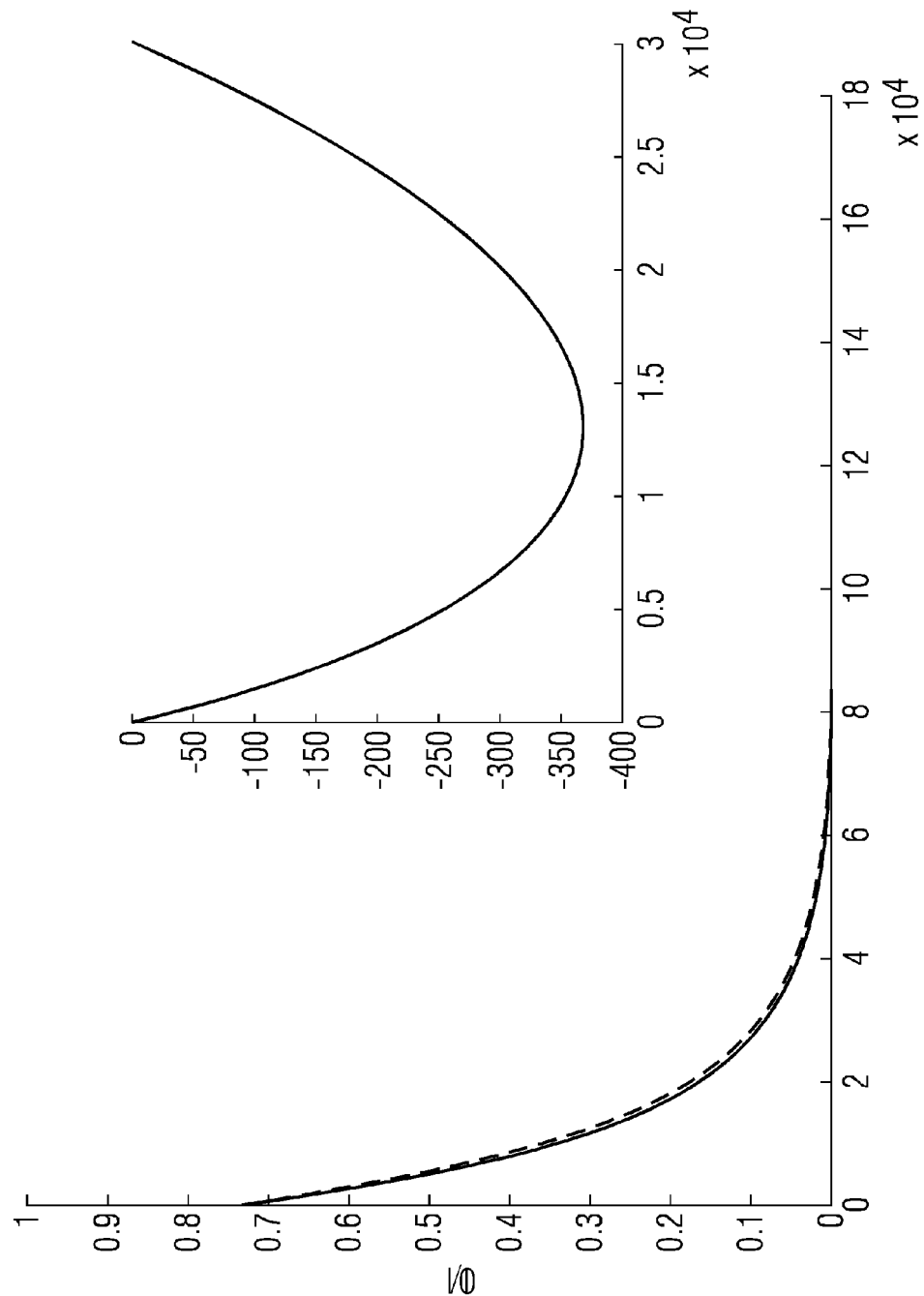
FIG. 7 is a graph of an exemplary embodiment of a correction of beam-hardening effects.

FIG. 7 shows an exemplary embodiment of a correction of beam-hardening effects, which are also described as Beam Hardening (BH). There takes place a simple beam-hardening correction for dark fields, wherein such a correction is already applied in a similar manner for a known CT, but in this case for complete CT projections. In the case of primary modulation, there arises a reinforced beam-hardening effect on the points of the dark fields, since the additional material that can be, for example, copper or tungsten, effects an additional hardening of the beam here, which does not occur in the light fields. With a simple simulation, it is possible to simulate theoretically exact attenuation curves for specific recording parameters (see Hammersberg and Mangard for this). A known limitation of this method is that, in the correction presented below, the theoretical exactitude only applies for mono-materials, i.e. only for objects to be recorded that consist of one material, which can be, for example, aluminum. If objects consisting of a plurality of materials, which are described as multi-materials, are examined, there will exist a somewhat large discrepancy compared to the actually occurring hardening effects. Two attenuation curves I/I0 are depicted in FIG. 7 for the example of the following recording parameters: Tube voltage 200 kV, tube-side pre-amplifier of 2 mm copper and object material of aluminum. Here, both curves show the ratio of the recorded signal to the complete signal, wherein a respective normalization to 1 is carried out. The ratio of the recorded signal to the complete signal is applied to the increasing penetration length by an aluminum wedge. Here, in the left-hand graph, the lower curve shows the case of light fields, wherein the pre-filtering of the spectrum actually only consists of 2.0 mm of copper. On the other hand, the upper curve reflects the case of dark fields, wherein a complete filter formed of 2.7 mm of copper is assumed. This means that, in addition to the tube-side pre-filter with a thickness of 2.0 mm, the additional material of the modulator in the dark fields, in this case 0.7 mm copper, is considered. The incident intensities, i.e. the intensities that are present after the modulator but before the object, are smaller for the dark fields than for the light fields. The radiation spectra behind the dark fields are still, on average, higher-energy, i.e. more strongly hardened, than the corresponding spectra behind the light fields. Due to this difference between the spectra, the radiation behind the dark fields penetrates the subsequent object material more effectively, and indeed relatively, so with respect to the same incident intensity. This influence is then considered by compensating for this effect for the dark fields by calculation. For the more strongly filtered 2.7 mm Cu spectrum (upper curve), there arises a relatively smaller attenuation than with the more weakly filtered 2.0 mm Cu spectrum (lower curve). According to a first embodiment, a beam-hardening correction is embodied before the scattering approximation. The dark fields of the modulated projection image are beam-hardening corrected during the underscanning, i.e. the value UncorrVal(m, n) measured in a dark field (m, n) is calculated by a value corrVal, which is calculated as follows:

$$\text{corrVal}(m, n) = \text{BHC}[\text{UncorrVal}(m, n) - \text{ApproxScatVal}(m, n)] + \text{ApproxScatVal}(m, n) \quad (1)$$

Firstly, an approximate scattering value ApproxScatVal(m, n) is derived from the measured value UncorrVal(m, n), which is generated from the most recently calculated scattered image of the preceding projection. This value is sought in the attenuation curve for the dark fields (upper curve); it corresponds to a certain penetration length. For this penetration length, a corresponding attenuation curve can now be found for the light fields (lower curve). This is depicted in the equation as function BHC[.]. Finally, the approximated scattering signal ApproxScatVal(m, n) is added again to this beam-hardening-corrected value. Thus, theoretically, the beam-hardening effect for the treated dark field (m, n) is completely compensated for.

In addition to the attenuation curves in a coordinate system, a second graph is depicted in FIG. 7 with a penetrated aluminum length of any unit along the abscissa and I/I0 as the normalized projection intensity along the ordinate, which graph specifies the correction values for the dark fields, i.e. the difference between both aforementioned attenuation curves, in grey tones, compared to an original grey tone in a dark field. Accordingly, from the second graph as well, based on an original grey tone in a dark field, this can be corrected by subtracting the corrected value.

According to a further advantageous embodiment, the correction of beam-hardening effects can also take place after the scattering approximation and before the division by the pure modulator image. To that end, the following must still be undertaken for a completely corrected CT projection after the scattering approximation. The scattered image that has just been calculated is subtracted from the original modulated CT projection. Then, pixel-by-pixel, a beam-hardening correction takes place for the dark fields, as is described in conjunction with formula (1). Here, it is considered individually for each pixel how much additional hardening material is available as a result of the modulator or the modulator field. According to the exemplary embodiment, these are between 0.0 and 0.7 mm of additional copper. In this way, by using a cone-beam computed tomograph, the edge pixels of the dark fields can also be corrected optimally, since, in such system geometry, the edges of the dark fields are not strictly delineated, in particular for off-centre fields, but rather have a gradual grey-tone path.

The use of a beam-hardening correction at two points in the method fundamentally improves, first of all, a scattering approximation, and indeed in particular for mono-materials with the first alternative of a beam-hardening correction and, second of all, leads to a complete correction of a modulator field pattern during division through the modulation field projection or modulation projection, and indeed in the second alternative of a beam-hardening correction, whereby ring artifacts in the CT volume can in turn be effectively reduced.

Figure 8:
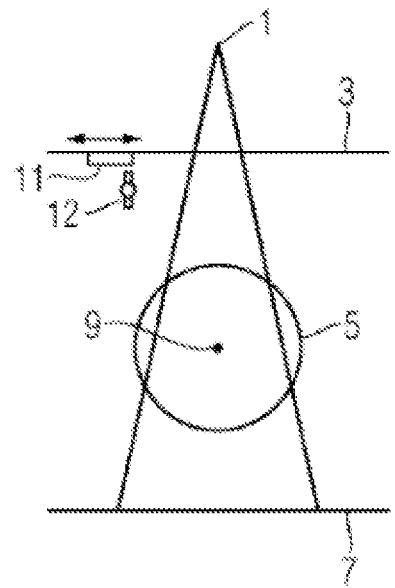
FIG. 8 is a schematic diagram of an exemplary embodiment of an apparatus.

FIG. 8 shows an exemplary embodiment of an apparatus. A primary signal or X-ray, which is depicted as a triangle, of a primary X-ray source 1 penetrates a modulator field 3 with a repeating pattern of regions with different levels of X-ray attenuation. Then the radiation penetrates an object 5 that is to be imaged, which is positioned rotatably around an axis of rotation 9. The result is an original, amplitude-modulated projection on a detector 7.

Figure 9A:
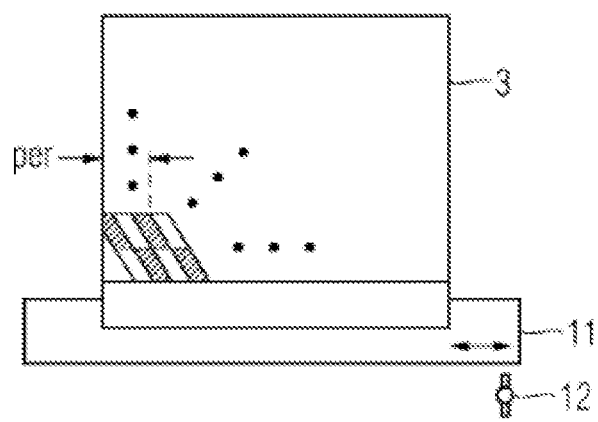
FIG. 9A is a schematic diagram of an exemplary embodiment of a modulator field.
Figure 9B:
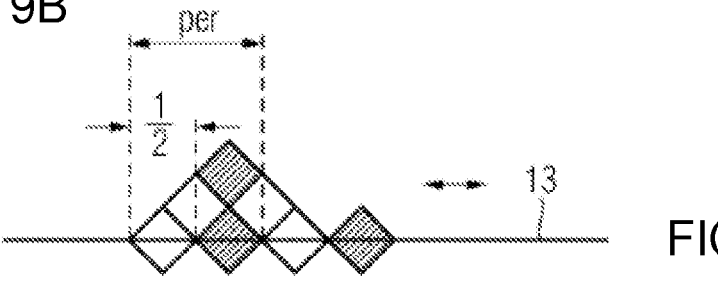
FIGS. 9B to 9D illustrate different patterns of modulator fields.
Figure 9C:
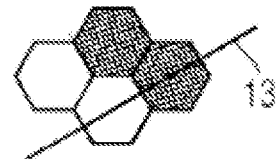
Figure 9D:
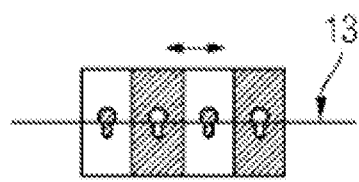

FIG. 9A shows an exemplary embodiment of a modulator field. Fundamentally, a displacement apparatus for the provision of a relative movement between X-ray source, object and detector on the one hand, and modulator field on the other, can be a linear motor for modulator fields, which is comparable to those according to FIGS. 3a to 4b, or a rotational motor for modulator fields, which is comparable to those according to FIGS. 5a and 5b. In the case of a linear modulator field, a linear motor 12 moves a linear table 11, which positions the modulator field 3. A modulator field 3 has a repeating pattern of regions with two different X-ray attenuation coefficients. A first half of the repeating pattern is congruent to a second half, wherein regions of both halves that are congruent to each other have opposite X-ray attenuation coefficients, the pattern is repeated along at least one repeating line 13, and a length of the pattern along the repeating line 13 corresponds to a period length per. FIG. 9A to 9D shows that, with a displacement movement of the modulator field 3 from a first position to a second position along the repeating line 13 at, for example, half a period length, modulator field regions with small and relatively large X-ray attenuation coefficients thereto are mutually exchanged. According to the present application, all patterns that provide the exchange described above are possible. Patterns with polygons are particularly suitable. FIGS. 9A to 9C show exemplary embodiments of modulator field patterns, such as parallelograms, rhombuses and hexagons. Furthermore, when polymers are used, it is possible to use halves of the patterns that have any respective shape within the polygons, as illustrated in FIG. 9D.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A method for correcting artifacts in an X-ray projection of an object, comprising:
    generating X-rays from a primary X-ray source with a repeating pattern of regions with different X-ray signal strengths to obtain amplitude modulated X-rays with temporal alterations;

detecting, by a detector as a complete signal, the amplitude-modulated X-rays after passing through the object to be imaged; and calculating a scattered image, separated from an original, amplitude-modulated projection, from the complete signal, such that a number (j=1 ... NMod) is generated from modulation projections allocated to a respective point in time.

2. The method as claimed in claim 1, wherein the primary X-ray source has individually activatable matrix regions which, at a previous point in time according to the repeating pattern, emit a small or a relatively large X-ray signal strength, and at a subsequent point in time emit a respective other X-ray signal strength, and at every point in time a respective original amplitude-modulated modulation projection of the object is generated and a respective scattered image allocated to this modulation projection is determined by said calculating.

3. The method as claimed in claim 1,
wherein said generating includes
arranging a modulator field, having regions corresponding to a repeating pattern of relatively small or large X-ray attenuation, in a beam path from the X-ray source to the object; and
moving at least one of the modulator field and together the X-ray source, the object and the detector, from a previous position to a subsequent position relative thereto, so that an X-ray beam from the primary X-ray source pass through modulator field regions with small and relatively large X-ray attenuation coefficients at different times,
wherein said detecting detects original amplitude-modulated modulation projections of the object generated in at least two positions of the modulator field relative to the X-ray source, the object and the detector, and
wherein said calculating determines the scattered image allocated to the modulation projections.

4. The method as claimed in claim 3, wherein said calculating obtains a scattering signal of a detector pixel or a scattered image of the detector by subtracting a primary signal or primary image that has been demodulated after temporal modulation from the complete signal or a complete image.

5. The method as claimed in claim 4, wherein said calculating further includes multiplication of a recorded complete signal with a modulation function.

6. The method as claimed in claim 5, wherein said calculating further includes subtraction of the scattered image assigned to the modulation projections to provide a scatter-corrected modulation projection, being carried out by a corresponding original modulation projection that has not been underscanned.

7. The method as claimed in claim 6, wherein said calculating further includes division of the scatter-corrected modulation projection to provide an additionally modulation-corrected modulation projection being effected by a temporal modulation function that is determined without the object.

8. The method as claimed in claim 7, further comprising
generating a respective scatter-corrected or scatter and modulator-field-corrected modulation projection for a respective number j=1 ... $N_{Mod}$ of modulations; and subsequently
averaging for increasing a signal-to-noise ratio.

9. The method as claimed in claim 8,
wherein previous and subsequent modulation generate a respective modulation projections j=1 and j=2 and
wherein said method further comprises rotating the X-ray source and detector together relative to the object around an axis of rotation in a rotational direction at an angle of rotation step from a relative position i to a relative position i+1.

10. The method as claimed in claim 9, further comprising underscanning for said calculating of the scattered image allocated to the modulation projections.

11. The method as claimed in claim 10, wherein said calculating further includes
calculating a primary image allocated to a modulation projection and having an individual primary signal for each pixel;
evaluating the complete signal for each pixel over all modulation projections j=1 ... N_ModProj as a temporal signal;
high-pass filtering the temporal signal;
demodulating, after said high-pass filtering by multiplication with the respective modulation function corresponding to the pixel; and
low-pass filtering after said demodulating to obtain a demodulated primary image.

12. The method as claimed in claim 11, wherein said calculating further includes subtracting the demodulated primary image allocated to the modulation projection from an averaged complete image to calculate a scattered image assigned to the modulation projection.

13. The method as claimed in claim 12, wherein said calculating further includes beam-hardening correction by
subtracting an approximated scattering value from a measured, uncorrected intensity value for beam-hardening correction for a respective modulation projection image field, which has been generated by a relatively small X-ray signal strength to obtain a difference corresponding to a first intensity value;
allocating the difference to a corresponding penetrated object length by a corresponding intensity attenuation curve;
allocating the penetrated object length to a second intensity value by an intensity attenuation curve for a modulation projection image field, which has been generated by a relatively high X-ray signal strength; and
adding the approximated scattering value to the second intensity value to obtain a correction value.

14. The method as claimed in claim 13, wherein said calculating further includes determining the approximated scattering value from a calculated scattered image of a previous original modulation projection.

15. The method as claimed in claim 14, wherein the beam-hardening correction is carried out during the underscanning.

16. The method as claimed in claim 14, wherein the beam-hardening correction is embodied by the temporal modulation function, before any division of the scatter-corrected modulation projection.

17. An apparatus for correcting artifacts in an X-ray projection of an object produced by X-rays from a primary X-ray source passing through a modulator field with a repeating pattern of regions with different X-ray attenuation for amplitude modulation, then passing through the object to be imaged to a detector which detects an original, amplitude-modulated projection, comprising:
a displacement apparatus moving the modulator field relative to the X-ray source, the object and the detector, from a previous position to a subsequent position along one of at least one repeating line of the repeating pattern in the modulator field, a first half of which is congruent to a second half, each of which have regions congruent to each other with the X-ray attenuation coefficients opposite to each other, the repeating pattern being repeated along at least one repeating line having a length corresponding to a period length, the modulator field having modulator field regions with relatively small and relatively large X-ray attenuation coefficients that are mutually exchanged in the X-ray path as the modulator field moves; and a processor calculating a scattered image separated from the original, amplitude-modulated projection.

18. The apparatus as claimed in claim 17, wherein further comprising a rotational apparatus synchronized with the displacement apparatus to rotate the object around an axis of rotation in a rotational direction at respective angle of rotation steps.

19. The apparatus as claimed in claim 18, wherein the pattern is one of a linear pattern, a square pattern, a wave-like pattern and a radial pattern.

20. The apparatus as claimed in claim 19, wherein the X-ray attenuation coefficients are changed continuously and consistently from transitions of first modulator field regions with relatively small X-ray attenuation coefficients to second modulator field regions with relatively large X-ray attenuation coefficients.

21. The apparatus as claimed in claim 20, wherein modulation strengths of the modulator field regions with the relatively large X-ray attenuation coefficient effect a complete signal reduction of 10% to 30%.

22. The apparatus as claimed in claim 21, wherein the modulator field has in addition to the first and second modulator field regions with the relatively small and relatively large X-ray attenuation coefficients, additional modulator field regions with additional X-ray attenuation coefficients.

* * * * *